US006270754B1

(12) United States Patent
Zhou et al.

(10) Patent No.: US 6,270,754 B1
(45) Date of Patent: *Aug. 7, 2001

(54) ANTIMICROBIAL CLEANING COMPOSITION

(75) Inventors: Boli Zhou, Antioch; Maria Ochomogo, Danville, both of CA (US)

(73) Assignee: The Clorox Company, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/345,735

(22) Filed: Jul. 1, 1999

Related U.S. Application Data

(63) Continuation of application No. 08/833,276, filed on Apr. 4, 1997, now Pat. No. 6,017,561.

(51) Int. Cl.[7] ............................... A61K 31/74; A61L 9/00; A61L 9/01; A01N 25/00
(52) U.S. Cl. ..................... 424/78.08; 424/76.1; 424/405; 424/486
(58) Field of Search ................... 424/76.1, 486, 424/424, 405, 78.08

(56) References Cited

U.S. PATENT DOCUMENTS

| | | | |
|---|---|---|---|
| 2,746,928 | 5/1956 | Darragh et al. | 252/106 |
| 2,804,728 | 9/1957 | Politzer et al. | 51/185 |
| 2,958,593 | 11/1960 | Hoover et al. | 51/295 |
| 3,080,688 | 3/1963 | Politzer | 51/185 |
| 3,093,591 | 6/1963 | Freese | 252/106 |
| 3,109,703 | 11/1963 | Politzer et al. | 18/59 |
| 3,142,714 | 7/1964 | Politzer et al. | 264/27 |
| 3,344,018 | 9/1967 | Shibe et al. | 167/22 |
| 3,471,423 | 10/1969 | Elmer et al. | 260/22 |
| 3,560,390 | 2/1971 | Gaines | 252/107 |
| 3,719,711 | 3/1973 | Temple | 260/257.6 |
| 3,793,275 | 2/1974 | Corey et al. | 260/28.5 |
| 4,110,429 * | 8/1978 | Gaffar et al. | 424/54 |
| 4,272,395 | 6/1981 | Wright | 252/106 |
| 4,476,251 | 10/1984 | Cianciolo et al. | 521/110 |
| 4,523,957 * | 6/1985 | Graf et al. | 106/277 |
| 4,576,729 | 3/1986 | Paszek et al. | 252/106 |
| 4,759,867 | 7/1988 | Choy et al. | 252/143 |
| 4,883,828 | 11/1989 | Oakes et al. | 523/122 |
| 4,908,381 | 3/1990 | Greenwald et al. | 424/78 |
| 4,935,232 | 6/1990 | McIntosh et al. | 424/78 |
| 5,028,619 | 7/1991 | Rei et al. | 514/372 |
| 5,061,485 | 10/1991 | Oakes et al. | 424/81 |
| 5,108,740 | 4/1992 | Greenwald et al. | 424/78.32 |
| 5,399,343 | 3/1995 | Smith, Jr. | 424/61 |
| 5,482,989 | 1/1996 | Koskiniemi | 524/404 |
| 5,728,505 * | 3/1998 | Dueber et al. | 430/271.1 |

FOREIGN PATENT DOCUMENTS

| | | |
|---|---|---|
| 63-301251 | 12/1988 | (JP) . |
| 02-225404 | 9/1990 | (JP) . |

OTHER PUBLICATIONS

"Reputex™20" Technical Information Bulletin, ZENECA Biocides, Wilmington, DE, May 1995.
"Reputex™20 Antibacterial/Antiodor Treatment for Cotton and Polyester" Technical Information Bulletin, ZENECA Biocides, Wilmington, DE, Oct. 1995.

* cited by examiner

Primary Examiner—Shelley A. Dodson
(74) Attorney, Agent, or Firm—Burns, Doane, Swecker & Mathis, L.L.P.

(57) ABSTRACT

A novel antibacterial cleaning composition which exhibits exceptional germicidal activity for sustained periods of time is provided. The antibacterial cleaning composition that includes: (a) a quaternary ammonium compound; (b) an anionic polymer having an acid number greater than 10 wherein the anionic polymer is partially or completely neutralized by the quaternary ammonium compound to form a polymer complex and wherein the polymer complex is greater than about 15% by weight of the solids in the composition; (c) a dispersing agent and/or solvent; and (d) water. The composition can be incorporated into the matrix of sponges. Alternatively, the quaternary ammonium compound can be complexed directly to cellulosic sponges that have been functionalized with anionic groups.

22 Claims, No Drawings

ANTIMICROBIAL CLEANING COMPOSITION

This application is a continuation, of application Ser. No. 08/833.276, filed Apr. 4, 1997, now U.S. Pat. No. 6,017,651.

FIELD OF THE INVENTION

The present invention relates generally to hard surface cleaners that are especially effective in household applications and particularly to an antimicrobial cleaning composition that exhibits exceptional and sustained germicidal activity.

BACKGROUND OF THE INVENTION

The use of quaternary ammonium compounds as an antibacterial agent is well known in the art. See U.S. Pat. Nos. 2,746,928, 3,344,018, 3,719,711, and JP 01/46081. For instance, quaternary ammonium compounds have been incorporated into polymer and liquid compositions to protect the compositions themselves from microbial attack. See U.S. Pat. Nos. 3,471,423, 5,028,619 and 5,399,343. Specifically, U.S. Pat. No. 5,399,343 discloses a nail lacquer composition, including a film forming polymer, in which the improvement comprises the inclusion of a carboxyl cellulose neutralized with an antimicrobial quaternary ammonium compound. This patent teaches that the polymer/quaternary ammonium compound complex be present in an amount no higher than 5% by weight of the solids in the composition. Furthermore, quaternary ammonium compounds have also been employed as an additive in a variety of household products including detergents. See U.S. Pat. Nos. 3,093,591, 3,560,390, 4,272,395 and 4,576,729. U.S. Pat. 4,476,251 discloses disposable polyurethane a wiping pad which apparently releases quaternary ammonium compounds that impart antibacterial activity.

Prior art antimicrobial products tend to exhibit rather weak germicidal activities. Endeavors to produce products demonstrating sustained activities include the use of polymer compositions which form purportedly abrasion resistant films containing biocides. See, for example, U.S. Pat. Nos. 3,793,275, 4,883,838, 4,908,381, 5,061,485, and 5,108,740. It is believed that these compositions are deficient in at least two respects. First, while the film may be wear-resistant, it rarely provides the desired antimicrobial activity. Second, the film may be difficult to remove thereby creating unsightly build-up problems.

SUMMARY OF THE INVENTION

The present invention is based on the discovery of a novel antibacterial cleaning composition which exhibits exceptional germicidal activity for sustained periods of time.

In one aspect, the invention is directed to an antibacterial cleaning composition that includes:

(a) a quaternary ammonium compound;
(b) an anionic polymer having an acid number greater than 10 wherein the anionic polymer is partially or completely neutralized by the quaternary ammonium compound to form a polymer complex and wherein the polymer complex is greater than about 15% by weight of the solids in the composition;
(c) a dispersing agent that is selected from the group consisting of a non-ionic polymer, a surfactant, a water-miscible solvent, and mixtures thereof;
(d) the balance, water.

In another aspect, the invention is directed to a method of imparting antibacterial action on a surface that includes the steps of:

(a) applying the inventive antibacterial cleaning composition onto the surface; and
(b) allowing water and solvent, if present, to evaporate from the cleaning composition to form a layer of said polymer complex that is coated on the surface. The polymer complex will provide sustained germicidal activity for the surface. However, the polymer complex can be readily removed if desired by wiping and washing the surface with detergent to prevent build-up problems. Preferably, the polymer complex comprises about 0.75% to 20% of the solids in the cleaning composition.

In a further aspect, the invention is directed to a cellulose material comprising anionic groups and quaternary ammonium compounds that are complexed to said anionic groups.

DETAILED DESCRIPTION OF PREFERRED EMBODIMENTS

The invention provides an antibacterial cleaning composition that forms a film on cleaned surfaces to prevent bacterial redeposition or recontamination. The cleaning composition is particularly suited for household hard surfaces especially in the bathroom and kitchen. However, it is understood that the cleaning composition can be applied on any surface or article such as fabrics. The aqueous formulation of the antibacterial cleaning composition generally comprises:

(a) a quaternary ammonium compound;
(b) an anionic polymer having an acid number greater than 10 wherein the anionic polymer is partially or completely neutralized by the quaternary ammonium compound to form a polymer complex and wherein the polymer complex is greater than about 15% by weight of the solids in the composition;
(c) a dispersing agent and/or a water-miscible solvent; and
(d) the balance, water.

In a preferred aqueous embodiment, the cleaning composition comprises approximately 0.05%–15% of an anionic polymer, 0.025%–8% of a quaternary ammonium compound, and a dispersing agent selected from (i) 0.02%–15% of a nonionic polymer, (ii) 1%–80% of a water miscible solvent, (iii) 0.05%–10% of a surfactant, or mixtures thereof, with the remainder, water. The anionic polymer preferably has an average molecular weight of about 2,000 to 1,000,000, and preferably an acid number larger than about 10. As used herein the term "acid number" retains its conventional meaning and is determined by the number of milligrams of potassium hydroxide required for the neutralization of the corresponding acids of the anionic groups present in one gram of the polymer.

In the cleaning composition, the anionic polymer is partially or completely neutralized by the quaternary ammonium compound to form a polymer complex. The cleaning composition is preferably prepared by mixing effective amounts of the anionic polymer and quaternary ammonium compound in water with agitation. The dispersing agent and/or water-miscible solvent is preferably added before the two main components all mixed together. As used herein of the term "dispersing agent" comprises any suitable agent which will cause the polymer complex to be stably distributed substantially homogeneously in the aqueous composition. Depending on the particular anionic polymers and quaternary ammonium compounds employed to synthesize the polymer complex, the presence of cross-linkers, and other variables, the polymer complex compositions may exist either as an emulsion, suspension, or solution. As used herein, the term "water-miscible solvent" or "solvent" refers to suitable organic solvents which can solubilize the polymer complex in the aqueous composition.

In use, the aqueous cleaning composition can be readily applied by conventional dispensing means. Preferably, the composition is sprayed or otherwise applied onto a surface to form an aqueous layer which develops into a polymer complex layer having sustained antimicrobial activity following evaporation of the water and solvent if present. Alternatively, the cleaning composition can be incorporated into a sponge or other suitable reusable article for applying the composition.

For ease of storage and transportation, water and solvent, if present, can be evaporated from the aqueous cleaning composition to form a gel of the polymer complex. The aqueous form can be reconstituted from the gel without any adverse effect on antibacterial action by dilution with water. Additional adjuncts in small amounts such as buffers, fragrance, dye and the like can be included to provide desirable attributes of such adjuncts.

In the specification, effective amounts are generally those amounts listed as the ranges or levels of ingredients in the descriptions which follow hereto. Unless otherwise stated, amounts listed in percentage ("%'s") are in weight percent (based on 100% active) of the cleaning composition.

1. Anionic Polymer

The anionic polymer is derived from monomers having anionic groups attached thereto. Preferably the polymer has an average molecular weight of about 2,000 to 1,000,000, and preferably from about 5,000 to 150,000, an acid number larger than about 10 and preferably from about 60 to 700.

Preferred anionic polymers are selected from the group consisting of: (1) a homopolymer that is selected from vinyl sulfonate, acrylate, methacrylate, styrene sulfonate, maleate, vinyl sulfate and mixtures thereof; (2) a copolymer that is derived from (i) one or more anionic monomers that are selected from the group consisting of vinyl sulfonate, acrylate, methacrylate, styrene sulfonate, maleate, vinyl sulfate (ii) one or more nonionic monomers that is selected from vinyl esters, vinyl alcohol, vinyl ethers, acrylamide, methacrylamide, alkyl or aryl acrylate, alkyl or aryl methacrylate, alkyl or aryl maleate, acrylonitrile, vinyl pyrrolidone, alkenes, such as, for example, styrene, ethylene and propylene, multifunctional acids, polyols, multifunctional amines, multifunctional isocyanates and multifunctional epoxy compounds; and (3) methylcarboxylate cellulose.

As is apparent, copolymers may comprise nonionic monomers. A preferred copolymer comprising nonionic and anionic is formed from acrylamide and acrylate monomers. The anionic polymers employed can be in their salt, acid or partially protonated forms.

The solubility of the anionic polymer will depend, in part, on its average molecular weight, acid number, and the solvent employed. In addition, the anionic polymer can be crosslinked with common crosslinkers such as, for example, carbodiimide, aziridine, polyols, glyoxal, epoxy compounds and transition metal ions, to reduce its solubility.

Typically, in formulating an aqueous antibacterial cleaning composition, the anionic polymer comprises about 0.05% to 15% and preferably about 0.1% to 8% of the composition.

2. Quaternary Ammonium Compound

Quaternary ammonium compounds are generally considered "broad spectrum" antimicrobial cationic compounds having efficacy against both gram positive (e.g., Staphylococcus sp.) and gram negative (e.g., *Escherichia coli*) microorganisms. Thus, the quaternary ammonium compound are incorporated for antibacterial purposes and should be present in amounts effective for such purposes.

The choice of the quaternary ammonium compounds is not critical. Typically they are preferably selected from mono-long-chain, tri-short-chain, tetralkyl ammonium compounds, di-long-chain, di-short-chain tetralkyl ammonium compounds, and mixtures thereof. By "long" chain is meant about $C_{6-30}$ alkyl. By "short" chain is meant $C_{1-5}$ alkyl, preferably $C_{1-3}$, or benzyl, or $C_{1-3}$ alkylbenzyl. Preferred materials include the BTC series (Stepan Company) such as BTC 2125, and the Barquat and Bardac series, such as Bardac 2250, from Lonza Chemical. The chains may straight or branched. N-heterocyclic ring compounds are also considered quaternary ammonia compounds.

Preferred quaternary ammonium compounds include, for example, $C_{8-22}$ dimethyl benzyl ammonium chloride, $C_{8-22}$ dimethyl ethylbenzyl ammonium chloride, and di $C_{6-20}$ alkyl dimethyl ammonium chloride.

Other appropriate quaternary ammonium compounds include paradiisobutylphenoxyethoxyethyl dimethyl benzyl ammonium chloride, and other compounds having a protonated N nucleus, such as chlorohexidine and poly (hexamethylene biguanide hydrochloride).

The anionic polymer is completely or partially neutralized by the quaternary ammonium compound to form a polymer complex which retains its antibacterial activity. Preferably, the polymer complex is greater than about 15%, and more preferably ranges from about 40% to about 100% by weight of the solids in the composition. The polymer complex is generally prepared by dissolving the anionic polymer in a solvent containing a dispersing agent, e.g, water and/or alcohol, and adding a desired amount of quaternary ammonium compound to form the polymer complex. Typically in formulating an aqueous antibacterial cleaning composition, the quaternary ammonium compound is about 0.025% to 8% and preferably about 0.1% to 5% of the composition. As is apparent, the amount of the quaternary ammonium compound adding will depend, in part, on the acid number of the anionic polymer.

3. Dispersing Agent

Liquid formulations of the antibacterial cleaning composition preferably comprise water and a dispersing agent that is selected from (i) a nonionic polymer, or (ii) a surfactant, or mixtures thereof. The amount of dispersing agent employed is not critical but preferably is present in an effective amount to emulsify or suspend the polymer complex in the liquid formulation.

A. Nonionic Polymer

Preferred nonionic polymers include, for example, polyvinyl alcohol, polyvinyl pyrrolidone, polyacrylamide, polyethylene oxide, polypropylene oxide, polyvinyl acetate, and mixtures thereof. Typically in formulating an aqueous antibacterial cleaning composition, the nonionic polymer is about 0.02% to 15% and preferably about 0.5% to 10% of the composition.

B. Surfactant

The surfactant is preferably a nonionic, amphoteric surfactant, or mixtures thereof. Typically in formulating an aqueous antibacterial cleaning composition, the surfactant is about 0.05% to 10% and preferably about 0.5% to 6% of the composition.

(i) Nonionic surfactants are preferably selected from alkoxylated alcohols, alkoxylated phenol ethers, and other surfactants often referred to as semi-polar nonionics, such as the trialkyl amine oxides. The alkoxylated phenol ethers include octyl- and nonylphenol ethers, with varying degrees of alkoxylation, such as 1–10 moles of ethylene oxide per mole of phenol. The alkyl group can vary from $C_{6-16}$, although octyl- and nonyl chain lengths are readily available. Various suitable products available from Union Carbide under the trademark Triton, such as Triton N-57, N-101, N-111, X-45, X-100, X-102, from Mazer Chemicals under the trademark Macol, from GAF Corporation under the trademark Igepal, and from Texaco Chemical Company under the trademark Surfonic. The alkoxylated alcohols include ethoxylated, and ethoxylated and propoxylated $C_{6-16}$ alcohols, with about 2–10 moles of ethylene oxide, or 1–10 and 1–10 moles of ethylene and propylene oxide per mole of alcohol, respectively. Exemplary surfactants are available from Shell Chemical under the trademark Neodol, and from Huntsman under the trademark Alfonic. The semi-polar amine oxides are also preferred, although, for the invention, a mixture of nonionic and amine oxide surfactants can also be used. The amine oxides, referred to as mono-long chain, di-short chain, trialkyl amine oxides, have the general configuration:

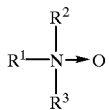

wherein $R^1$ is $C_{6-24}$ alkyl, and $R^2$ and $R^3$ are both $C_{1-4}$ alkyl, or $C_{1-4}$ hydroxyalkyl, although $R^2$ and $R^3$ do not have to be equal. These amine oxides can also be ethoxylated or propoxylated. The preferred amine oxide is lauryl amine oxide. The commercial sources for such amine oxides are Barlox 10, 12, 14 and 16 from Lonza Chemical Company, Varox by Witco and Ammonyx by Stepan Co.

Other preferred nonionic surfactants include ethoxylated fatty acid esters which are available under the trademark Ethox from Ethox Chemicals, Inc., sorbitan derivatives available under the trademark Tween from ICI Surfactants, and glycerol esters which are available under the trademark Polyaldo from Lonza.

A further preferred semi-polar nonionic surfactant is alkylamidoalkylenedialkylamine oxide. Its structure is shown below:

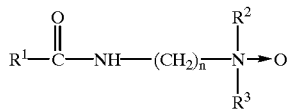

wherein $R^1$ is $C_{5-20}$ alkyl, $R^2$ and $R^3$ are $C_{1-4}$ alkyl,

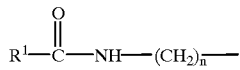

or $-(CH_2)_p-OH$, although $R^2$ and $R^3$ do not have to be equal or the same substituent, and n is 1–5, preferably 3, and p is 1–6, preferably 2–3. Additionally, the surfactant could be ethoxylated (1–10 moles of EO/mole) or propoxylated (1–10 moles of PO/mole). This surfactant is available from various sources, including from Lonza Chemical Company, as a cocoamidopropyldimethyl amine oxide, sold under the brand name Barlox C. Additionally semi-polar surfactants include phosphine oxides and sulfoxides.

(ii) The amphoteric surfactant is typically an alkylbetaine or a sulfobetaine. One group of preferred amphoterics are alkylamidoalkyldialkylbetaines. These have the structure:

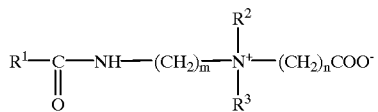

wherein $R^1$ is $C_{6-20}$ alkyl, $R^2$ and $R^3$ are both $C_{1-4}$ alkyl, although $R^2$ and $R^3$ do not have to be equal, and m can be 1–5, preferably 3, and n can be 1–5, preferably 1. These alkylbetaines can also be ethoxylated or propoxylated. The preferred alkylbetaine is a cocoamidopropyldimethyl betaine called Lonzaine CO, available from Lonza Chemical Co. Other vendors are Henkel KGaA, which provides Velvetex AB, and Witco Chemical Co., which offers Rewoteric AMB-15, both of which products are cocobetaines.

4. Water-miscible Solvent

Instead of or, in addition to, using the dispersing agent, a water-miscible solvent to solubilize the polymer complex can be employed. The water-miscible solvent is preferably selected from $C_{1-6}$ alkanol, $C_{1-6}$ diols, $C_{3-24}$ alkylene glycol ethers, and mixtures thereof. The alkanol can be selected from methanol, ethanol, n-propanol, isopropanol, butanol, pentanol, hexanol, their various positional isomers, and mixtures of the foregoing. It may also be possible to utilize in addition to, or in place of, said alkanols, the diols such as ethylene, propylene and butylene glycols, and mixtures thereof. Preferred solvents that may be used include ethanol, isopropyl alcohol, butanol, amyl alcohol, ethylene glycol ethers, acetone and propylene glycol ethers.

The alkylene glycol ether solvents can include ethylene glycol monobutyl ether, ethylene glycol monopropyl ether, propylene glycol n-propyl ether, propylene glycol monobutyl ether, diethylene glycol n-butyl ether, dipropylene glycol methyl ether, and mixtures thereof. Preferred glycol ethers are ethylene glycol monobutyl ether, also known as butoxyethanol, sold as butyl Cellosolve by Union Carbide, and also sold by Dow Chemical Co., 2-(2-butoxyethoxy) ethanol, sold as butyl Carbitol, also by Union Carbide, and propylene glycol n-propyl ether, available from a variety of sources. Another preferred alkylene glycol ether is propylene glycol, t-butyl ether, which is commercially sold as Arcosolve PTB, by Arco Chemical Co. Typically in formulating an aqueous antibacterial cleaning composition, the water-miscible solvent is about 1% to 80% and preferably about 5% to 50% of the composition.

5. Water and Miscellaneous

For liquid formulations, the antibacterial cleaning composition is most preferably an aqueous formulation comprising at least about 15%, and more preferably at least about 40% water.

Furthermore, small amounts of adjuncts can be added for improving cleaning performance or aesthetic qualities of the cleaner. For example, buffers could be added to maintain a constant pH preferably between about 1.5–14, more preferably between about 8–13. These buffers include NaOH, KOH, $Na_2CO_3$, $K_2CO_3$, as alkaline buffers, and phosphoric, hydrochloric, sulfuric acids as acidic buffers, and others. Builders, such as phosphates, silicates, carbonates, sodium chloride, and magnesium chloride, may be desirable. Further solubilizing materials, such as hydrotropes, e.g., cumene, toluene and xylene sulfonates, may also be desirable. Adjuncts for cleaning include additional surfactants, such as those described in *Kirk-Othmer, Encyclopedia of Chemical Technology*, 3rd Ed., Volume 22, pp. 332–432 (Marcel-Dekker, 1983), and *McCutcheon's Soaps and Detergents* (N.

Amer. 1984), which are incorporated herein by reference. Aesthetic adjuncts include fragrances, such as those available from Givaudan, IFF, Quest, Sozio, Firmenich, Dragoco and others, and dyes and pigments which can be solubilized or suspended in the formulation, such as diaminoanthraquinones. Water-insoluble solvents may sometimes be desirable as added grease or oily soil cutting agents. These types of solvents include tertiary alcohols, hydrocarbons (alkanes), pine-oil, d-limonene and other terpenes and terpene derivatives, and benzyl alcohols. Thickeners, such as calcium carbonate, sodium bicarbonate, aluminum oxide, and polymers, such as polyacrylate, starch, xanthan gum, alginates, guar gum, cellulose, and the like, may be desired additives. The use of some of these thickeners ($CaCO_3$ or $NaHCO_3$) is to be distinguished from their potential use as builders, generally by particle size or amount used.

The antibacterial cleaning composition may further include an adhesion promoter such as, for example, a hydroxyl silicone which serves to bind the polymer complex to a surface.

Incorporation of Polymer Complex or Quaternary Ammonium Compound into Sponge.

The antibacterial cleaning composition can be incorporated into pads or other similar reusable articles having an absorbent and/or adsorbent matrix. It is advantageous to incorporate the antibacterial composition, since this will prevent or mitigate the microbial contamination of such matrix. Preferably, the pads are made from natural and synthetic sponges, e.g., cellular plastic, foam, and rubber sponge. Preferred commercially available synthetic sponges include polyurethane and cellulose sponges. Cellulose sponges are typically derived from regenerated cellulose. One method of incorporating the antibacterial cleaning composition is to treat (e.g. soak) the sponge in the liquid formulation and thereafter allow the sponge to dry. The dry polymer complex residue or layer becomes attached to or associated with the sponge surfaces. Attachment or association occurs through weak non-chemical bonds.

Alternatively, after soaking the sponge in the liquid formulation, excess formulation can be removed from the sponge and thereafter the sponge can be stored in a moist state for later use without further drying.

Another method of incorporating the polymer complex into a sponge, e.g., a cellulose sponge is to impregnate a mass of cellulose material with the anionic polymer. By impregnation is meant that the anionic polymer is thoroughly mixed into the cellulose material. Thereafter, the impregnated cellulose material is placed into contact with an aqueous solution containing the quaternary ammonium compound whereby the polymer complex is formed. Alternatively, the polymer complex can be fabricated first and thereafter it is impregnated into the cellulose mass.

In addition, the sponge, or other absorbent/adsorbent substrate, can have an abrasive action, either through incorporation within the absorbent/adsorbent matrix (see Hoover, U.S. Pat. No. 2,958,593), or as an abrasive surface or scrim (see Politzer, U.S. Pat. Nos. 2,804,728, 3,080,688, 3,109, 703, and 3,142,714; and co-pending application Ser. No. 08/532,532, filed Sep. 22, 1995, entitled "Scrubbing Device Comprising a Woven Scrim and Adsorbent Body," of Michael C. Fryan; all of the foregoing are incorporated by reference thereto).

A further method of impregnating the sponge is to expose the sponge to an aqueous mixture containing the anionic polymer for a sufficient amount of time to allow the polymer to become attached to the sponge surface and thereafter adding the quaternary ammonium compound to the mixture.

A method of fabricating a sponge with antibacterial properties is to complex quaternary ammonium compounds directly onto cellulosic sponges that have been functionalized with anionic groups. For example, a sponge comprising a negatively-charged cellulosic sponges can be derived by a reaction of a chemical agent having a molecular formula of XRY (X=leaving groups such as, for example Cl, Br, $OSO_3^-$); R=organic moiety; Y=anionic groups such as COONa) with the sponge cellulose. An example of the XRY is $ClCH_2COONa$.

Methods for regenerating cellulose to make porous sponges are known in the art. For example, a viscose cellulose material may be formed by steeping sheets of cellulose in 18½% (by weight) sodium hydroxide solution for a time sufficient to alkalize the cellulose. The resulting alkaline cellulose is mixed with carbon disulfide, for example, and the resulting mixture is agitated until cellulose xanthate is produced. This resulting cellulose xanthate is dissolved in a weak sodium hydroxide solution to produce a viscose cellulose product, typically containing between 5% and 7% by weight cellulose, 5% to 6% of alkalinity and about 2.3% to 2.6% total sulphur. This unripened material may be mixed with hemp fibers or other suitable reinforcing fibers, typically having an average length of about ⅜ to ½ an inch, (0.95 to 1.27 cm) while maintaining the mass at a temperature preferably below about 15° C. for about 20 minutes. To this mass is added sodium sulfate decahydrate crystals, having an average particle size in accordance with the desired pore size of the finished sponge. Typically, an average particle size of the sodium sulfate decahydrate of about 10 mm will produce a relatively course pore device, whereas an average particle size of about 2 mm will produce a relatively fine pore device,. The mixing is continued for approximately an additional ten minutes while maintaining a temperature of 15° C. or less. This mass may then be deposited into molds or forms of any desirable configuration, preferably rectilinear, and coagulated.

The coagulated cellulose sponge may then be washed in hot water to remove the remaining sodium sulfate decahydrate, neutralized in base, such as sodium sulfate decahydrate, neutralized in base, such as sodium hydroxide solution, and bleached with a water solution containing hypochlorite. The bleached blocks may then be treated in hot oxalic acid and again washed to remove traces of []he acids. The blocks or sheets may then be sprayed with a humectant such as glycerin, PEG, propylene glycol, urea or mixtures thereof and dried to the desired moisture content.

EXPERIMENTAL

In the following experiments, the inventive antimicrobial cleaning compositions were tested with respect to antimicrobial activity and delivery efficiency. In Examples 1–2, aqueous formulations comprising the components set forth in Table 1 were tested.

TABLE 1

| | Formulation | | |
|---|---|---|---|
| Component | 1 | 2 | 3 |
| Copolymer of acrylamide and sodium acrylate (72:28)[1] | 2.4% | — | — |
| Polyvinyl pyrolidone | — | — | 6.0% |
| Sodium polyvinyl sulfonate[2] | 0.18% | 0.18% | — |

TABLE 1-continued

| | Formulation | | |
|---|---|---|---|
| Component | 1 | 2 | 3 |
| Sodium polyacrylate copolymer[3] | — | — | 0.63% |
| $C_{14}$ tetralkyl NCl | 0.5% | 0.5% | 0.5% |

[1]Glascol WN15/25 (Allied Colloids)
[2]PSVS (Air Products)
[3]Carboset GA 1915 (BF Goodrich)

EXAMPLE 1

Antibacterial Activity

Black colored ceramic tiles each having a surface area of 1 in.$^2$ (6.45 cm$^2$) were initially sterilized before 0.07 grams of a formulation were sprayed onto the surface of each tile. The tiles were allowed to dry for at least 12 hours before being initially inoculated with 10 μl of a test organism suspension which provided an initial load of at least 10$^6$ bacteria on the surface. For the zero hour readings, the bacterial population was measured after 10 minutes of contact time. For later analyses, each tile was rinsed and re-inoculated at intervals so that after 24, 48, and 72 hours, a tile would have been rinsed and reinoculated 1, 3, and 4 times, respectively. For each rinse, a spray bottle with the nozzle positioned approximately 10 to 12 inches (25.4 to 30.5 cm) from the surface of a tile held upright was used. The tile was sprayed with water for about 5 minutes. Following each rinse the tile was re-inoculated with 10 μl of the test organism suspension. Finally, following the last rinse and re-inoculation, each tile was allowed to incubate for a period up to about 12 hours before being inoculated for a final time. Thereafter, about 10 minutes later, the bacterial population was measured. For example, tiles initially incubated for 72 hours underwent 4 rinses and re-inoculations. Following the fourth and final rinse/re-inoculation cycle, the tile was subject to one final inoculation as described above before the bacterial population was measured.

The bacterial survival ratio (R) is the ratio of bacterial population for the inoculated versus that of an untreated tile. The percentage reduction of bacteria for each sample is set forth in Table 2 is defined as 1 minus R. As is apparent from the data, the inventive antibacterial cleaning composition provided exceptional long lasting antibacterial activity as compared to a commercial cleaner.

TABLE 2

| | Reduction of Bacteria (%) | | | | | |
|---|---|---|---|---|---|---|
| | Gram-positive bacteria (S. aureus) | | | Gram-negative bacteria (K. pneumoniae) | | |
| Formulation | 0-hr/ no rinse | 24-hrs/ 1 rinse | 72 hrs/ 4 rinses | 0-hr/ no rinse | 24-hrs/ 1 rinse | 48 hrs/ 3 rinses |
| 1 | >99.998 | — | >99.995 | >99.998 | — | >99.951 |
| 2 | >99.998 | 99.970 | — | >99.999 | 99.976 | — |
| 3 | 99.997 | 99.135 | — | >99.999 | 99.96 | — |
| CAP[1] | 99.998 | 0.0 | — | 99.41 | 0.0 | — |

[1]Commercial Antimicrobial Product. (Active ingredients: quaternary ammonium compound, solvent and water)

EXAMPLE 2

Antibacterial Activity

Formulation 1 from Table 2 was applied onto tiles in the same manner as in Example 1 except that prior to inoculation with K. pneumoniae the tiles were immersed in a bath containing 50 ml of water for 3 minutes. Thereafter, the bacterial population of the tiles (without any incubation) were measured. The percentage of reduction for bacterial was about 99.49%. In contrast, similarly tested tiles sprayed with the Commercial Antimicrobial Product exhibited essentially 0% reduction.

EXAMPLE 3

Antibacterial Activity of Sponge Delivery System

Various aqueous formulations of the inventive cleaning composition having the components set forth in Table 3 were incorporated into cellulose sponges. The sponges employed were each about 5×7×1 (in.) (12.7×17.78×2.54 (cm)) in dimension. For formulations 1–4, 100 grams of the formulation were soaked into sponges which were then air dried. For formulation 5, the sponge was soaked into 100 grams of a solution containing the anionic polymer. The sponge was then air dried. Next, the sponge was soaked into 100 grams of an aqueous solution containing the quaternary ammonium component and crosslinking agent (glyoxal). Thereafter, the sponge was air dried. For formula 6, the sponge was soaked into 100 grams of a solution containing the antibacterial cleaning formulation. Thereafter, enough solution was removed so that the sponge contained approximately 20 grams of the aqueous antibacterial cleaning formulation remaining therein. The moist sponge was stored in a plastic bag.

TABLE 3

| | Formulation | | | | | |
|---|---|---|---|---|---|---|
| Component | 1 | 2 | 3 | 4 | 5 | 6 |
| $C_{12-16}$ benzyl dimethyl NCl[1] | 1.3% | — | 1.3% | — | 1.3% | — |
| $DiC_{10}$ di-methylNCl[2] | — | 1.3% | — | 1.3% | — | 2% |
| Sodium polyvinyl sulfonate | 0.47% | 0.47% | — | — | — | 0.42% |
| Sodium polyacrylate[3] | — | — | 0.37% | — | — | — |
| Polyacrylic acid[4] | — | — | — | 0.37% | — | — |
| Copolymer of acrylic acid and acrylamide[5] | — | — | — | — | 0.61% | — |
| Copolymer of acrylamide and sodium acrylate[6] | — | — | — | — | — | 2.6% |
| Glyoxal[7] | — | — | — | — | 0.07% | — |
| $NaCO_3$ | — | — | — | — | 0.3% | — |
| Isopropyl alcohol | 40% | 40% | 40% | 40% | — | — |

[1]Barquat MB-50 (Lonza)
[2]Bardac 2280 (Lonza)
[3]Acusol 504N (Rhom & Haas)
[4]Glascol E11 (Allied Colloids)
[5]Glascol WN-33 (Allied Colloids)
[6]Glascol WN 15/25 (Allied Colloids)
[7](Aldrich Chemical)

Sponges designated 1–5 which correspond to the particular antibacterial formulation which is incorporated therein were tested for their ability to deliver antibacterial activity. The sponges were subject to one of three water pretreatment regiments: (1) a pre-rinse, (2) squanching, or (3) machine wash. In the pre-rinse, a sponge was placed into approximately 300 ml of water and allowed to soaked with water. Excess water was then manually squeezed from the sponge.

This was repeated 5 times with fresh water. In squanching, a proprietary and automated device which included a chamber and rotable arm that included a presser that held the sponge was employed. Water continuously flowed through the sponge during the squanching procedure. The cyclic movement of the arm pressed the sponge against a surface of the container. Ivory dish detergent (Procter & Gamble) was applied to the sponge at the beginning of the procedure and after the first 500 cycles. Squanching lasted for about 20 minutes after about 2000 cycles of the arm. Finally, a regular washing machine was used in the last pretreatment. Each sponge was subject to 2 full wash cycles. The first was with detergent and the second without.

Sponges were inoculated with bacteria that comprise a composite of *S. aureus, P. aruginosa, E. coli,* and *S. choleraesuis*. After inoculation the sponges were placed in plastic bags at 30° C. for 24 hours. The bacteria population for the sponges were measured before ($I_o$) and after ($I_f$) incubation. As is apparent from the data in table 4, the sponges maintain antibacterial activity even after being subjected to the pre-rinsing, squanching, and machine washing.

TABLE 4

| Test No. | Sponge | Pre-rinsed | Squanched | Machine washed | $I_o$ | $I_f$ |
|---|---|---|---|---|---|---|
| 1 | 1 | yes | — | — | $1.7 \times 10^6$ | <10 |
| 2 | 1 | — | yes | — | $1.1 \times 10^6$ | <10 |
| 3 | 1 | — | — | yes | $1.8 \times 10^6$ | $3.0 \times 10^5$ |
| 4 | 2 | yes | — | — | $1.6 \times 10^6$ | <10 |
| 5 | 2 | — | yes | — | $1.2 \times 10^6$ | <10 |
| 6 | 3 | yes | — | — | $1.1 \times 10^6$ | <10 |
| 7 | 3 | — | yes | — | $1.7 \times 10^6$ | $2.0 \times 10^4$ |
| 8 | 4 | yes | — | — | $1.6 \times 10^6$ | 100 |
| 9 | 4 | — | yes | — | $1.6 \times 10^6$ | $4.0 \times 10^3$ |
| 10 | 5 | yes | — | — | $1.5 \times 10^6$ | <10 |
| 11 | 5 | — | yes | — | $1.0 \times 10^6$ | $6.0 \times 10^3$ |
| 12 | 6 | — | yes | — | $1.1 \times 10^6$ | $6.8 \times 10^3$ |
| 13 | untreated sponge | — | — | — | $1.6 \times 10^6$ | $6.0 \times 10^8$ |

EXAMPLE 4

Odor Control of Sponge Delivery System

Aqueous formulations 1–5 of the antibacterial cleaning composition set forth in Table 5 were incorporated into cellulose sponges by the single soaking step as described in Example 3. For aqueous formula 6, the antibacterial cleaning composition was incorporated by soaking the sponge in 100 grams of the composition and thereafter squeezing excess composition from the sponge. The moist sponge was stored in a plastic bag before being used.

TABLE 5

| | Formulation | | | | | |
|---|---|---|---|---|---|---|
| Component | 1 | 2 | 3 | 4 | 5 | 6 |
| C12–16 benzyl dimethyl NCl[1] | 1.3% | — | 1.0% | 1.3% | 1.3% | — |
| DiC$_{10}$ dimethylNCl[2] | — | 1.0% | — | — | — | 2% |
| Sodium polyvinyl sulfonate | 0.47% | 0.36% | 0.36% | — | — | — |
| Sodium polyacrylic acid[3] | — | — | — | 0.48% | 0.48% | 0.42% |
| Copolymer of acrylic acid and acrylamide[4] | — | 1.3% | 2.6% | — | — | — |
| Copolymer of acrylamide and sodium acrylate | — | — | — | — | — | 2.6% |
| Isopropyl alcohol | 40% | — | — | — | — | — |
| Multifunctional carbodimide[6] | — | — | — | 0.39% | 0.1% | — |
| HCl | — | — | — | 0.033% | 0.033% | — |

[1]Barquat MB-50 (Lonza)
[2]Bardac 2280 (Lonza)
[3]Glascol E11 (Allied Colloids)
[4]Glascol WN-15/25 (Allied Colloids)
[5]Glascol WN 15/25 (Allied Chemicals)
[6]Ucarlink (Union Carbide)

The sponges were subject to squanching as described in Example 3. Each sponge was then inoculated with a bacterial composite comprising *E. aerogenes, P. aruginosa, P. mirabilis, S. aureus* and 1% nutrient. Thereafter the sponge was incubated in a plastic bag at 30° C. for 24 hours.

The sponges were graded by a panel of expert graders to determined whether the sponges significantly reduced odor as compared to biocideless sponges. All sponges treated with the antibacterial cleaning composition demonstrated odor reduction as compared to untreated sponges which did not.

The foregoing has described the principles, preferred embodiments and modes of operation of the present invention. However, the invention should not be construed as being limited to the particular embodiments discussed. Thus, the above-described embodiments should be regarded as illustrative rather than restrictive, and it should be appreciated that variations may be made in those embodiments by workers skilled in the art without departing from the scope of the present invention as defined by the following claims.

What is claimed is:

1. An antibacterial cleaning composition comprising:
   (a) a quaternary ammonium compound;
   (b) an anionic polymer having an acid number greater than 10 wherein the anionic polymer and the quaternary ammonium form a polymer complex wherein the polymer complex is greater than about 15% by weight of the solids in the composition and wherein the average molecular weight of the anionic polymer ranges from greater than about 5,000 to about 1,000,000;
   (c) optionally a dispensing agent; and
   (d) optionally, a solvent.

2. The cleaning composition of claim 1 wherein the polymer complex comprises about 15% to 100% of the solids in the composition.

3. The cleaning composition of claim 1 wherein the anionic polymer has an acid number that ranges from about 60 to 700.

4. The cleaning composition of claim 1 wherein the a quaternary ammonium compound is selected from the group consisting of $C_{8-22}$ dimethyl benzyl ammonium chloride, $C_{8-22}$ dimethyl ethylbenzyl ammonium chloride, di $C_{6-20}$ alkyl dimethyl ammonium chloride, paradiisobutylphenoxyethoxyethyl dimethyl benzyl ammonium chloride, chlorohexidine and poly(hexamethylene biguanide hydrochloride), and mixtures thereof.

5. The cleaning composition of claim 1 wherein the anionic polymer is selected from the group consisting of: (1) a homopolymer that is selected from vinyl sulfonate, acrylate, methacrylate, styrene sulfonate, maleate, vinyl sulfate and mixtures thereof; (2) a copolymer that is derived from (i) one or more anionic monomers that are selected from the group consisting of vinyl sulfonate, acrylate, methacrylate, styrene sulfonate, maleate, vinyl sulfate (ii) one or more nonionic monomers that are selected from vinyl esters, vinyl alcohol, vinyl ethers, acrylamide, methacrylamide, alkyl or aryl acrylate, alkyl or aryl methacrylate, alkyl or aryl maleate, acrylonitrile, vinyl pyrrolidone, alkenes, multifunctional acids, polyols, multifunctional amines, multifunctional isocyanates, multifunctional epoxies, and mixtures thereof, and (3) methylcarboxylate cellulose.

6. The cleaning composition of claim 1 wherein the nonionic polymer is selected from the group consisting of polyvinyl alcohol, polyvinyl pyrrolidone, polyacrylamide, polyethylene oxide, polypropylene oxide, polyvinyl acetate, and mixtures thereof.

7. The cleaning composition of claim 1 wherein the cleaning composition is an aqueous composition which comprises a dispersing agent that is selected from the group consisting of a surfactant, nonionic polymer, and mixtures thereof.

8. The cleaning composition of claim 1 wherein the anionic polymer is crosslinked with a crosslinker that is selected from the group consisting of carbodiimide, aziridine, polyol, glyoxal, epoxy, transition metal ion, and mixtures thereof.

9. The cleaning composition of claim 1 wherein the cleaning composition is an aqueous composition which comprises a dispersing agent that is a surfactant that is selected from the group consisting of nonionic surfactant, amphoteric surfactant, and mixtures thereof.

10. The cleaning composition of claim 1 wherein the cleaning composition is an aqueous composition which comprises a water-miscible solvent that is selected from the group consisting of ethanol, isopropyl alcohol, butanol, amyl alcohol, ethylene glycol ether, acetone, propylene glycol ether, and mixtures thereof.

11. The cleaning composition of claim 1 wherein the cleaning composition is an aqueous composition which comprises a dispersing agent that comprises a nonionic polymer that is selected from the group consisting of polyvinyl alcohol, polyvinyl pyrrolidone, polyacrylamide, polyethylene oxide, polypropylene oxide, polyvinyl acetate, and mixtures thereof.

12. The cleaning composition of claim 1 further comprises an adhesion promoter.

13. The cleaning composition of claim 1 wherein the composition is an aqueous mixture.

14. The cleaning composition of claim 1 wherein the composition is a gel.

15. The cleaning composition of claim 1 wherein the composition comprises:
    (a) about 0.026% to 8% of a quaternary ammonium compound;
    (b) about 0.05% to 15% of an anionic polymer;
    (c) either (i) a dispersing agent selected from about 0.02% to 15% of a nonionic polymer or about 0.05% to 10% of a surfactant, or (ii) about 1% to 80% of a water-miscible solvent; and
    (d) the balance, water.

16. The cleaning composition of claim 16 where the polymer complex comprises about 15% to 100% of the solids in the composition.

17. A method of rendering a surface with residual antibacterial action that comprises the steps of:
    (a) applying an antibacterial cleaning composition onto the surface wherein the cleaning composition comprises:
        (i) a quaternary ammonium compound;
        (ii) an anionic polymer having an acid number greater than 10 wherein the anionic polymer and the quaternary ammonium compound form a polymer complex wherein the polymer complex is greater than about 15% by weight of the solids in the composition and wherein the average molecular weight of the anionic polymer ranges from greater than about 5,000 to about 1,.000,000 wherein;
        (iii) either (1) a dispersing agent selected from a nonionic polymer or a surfactant, or (2) a water-miscible solvent; and
        (iv) the balance, water; and
    (b) allowing water and solvent, if present, to evaporate from the cleaning composition to form a layer of said polymer complex that is coated on the surface.

18. The cleaning composition of claim 1 wherein the average molecular weight of the anionic polymer ranges up to about 150,000.

19. The cleaning composition of claim 1 wherein the average molecular weight of the anionic polymer ranges from 150,000 to 1,000,000.

20. The cleaning composition of claim 17 wherein the anionic polymer has an acid number that ranges from about 60 to 700.

21. The cleaning composition of claim 17 wherein the average molecular weight of the anionic polymer ranges up to about 150,000.

22. The cleaning composition of claim 17 wherein the average molecular weight of the anionic polymer ranges from 150,000 to 1,000,000.

* * * * *